(12) United States Patent
Johnson et al.

(10) Patent No.: US 8,317,800 B2
(45) Date of Patent: Nov. 27, 2012

(54) INJECTABLE MATERIAL DELIVERY DEVICE WITH AN INTEGRATED MIXER

(75) Inventors: Michael Johnson, West Olive, MI (US); Jon Moroney, Grand Haven, MI (US); Joseph J Saladino, Memphis, TN (US); Aashiish Agnihotri, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1064 days.

(21) Appl. No.: 12/107,373

(22) Filed: Apr. 22, 2008

(65) Prior Publication Data
US 2009/0264816 A1 Oct. 22, 2009

(51) Int. Cl.
*A61M 37/00* (2006.01)

(52) U.S. Cl. .......................... 606/93; 366/252

(58) Field of Classification Search ............... 606/92–94; 366/242, 247, 326.1
See application file for complete search history.

(56) References Cited

U.S. PATENT DOCUMENTS

| | | | |
|---|---|---|---|
| 4,787,751 A | 11/1988 | Bakels | |
| 4,961,647 A | 10/1990 | Coutts | |
| 4,973,168 A | 11/1990 | Chan | |
| 5,075,234 A * | 12/1991 | Tunac | 366/102 |
| 5,100,241 A | 3/1992 | Chan | |
| 5,193,907 A | 3/1993 | Faccioli | |
| 5,368,386 A | 11/1994 | Murray | |
| 5,435,645 A | 7/1995 | Faccioli | |
| 5,494,349 A | 2/1996 | Seddon | |
| 5,514,135 A | 5/1996 | Earle | |
| RE35,276 E | 6/1996 | Chan | |
| 5,531,519 A | 7/1996 | Earle | |
| 5,545,460 A | 8/1996 | Tanaka | |
| 5,571,282 A | 11/1996 | Earle | |
| 5,588,745 A | 12/1996 | Tanaka | |
| 5,797,678 A | 8/1998 | Murray | |
| 5,797,679 A | 8/1998 | Grulke | |
| 5,842,785 A | 12/1998 | Brown | |
| 5,975,751 A | 11/1999 | Earle | |
| 6,024,480 A | 2/2000 | Seaton | |
| 6,042,262 A | 3/2000 | Hajianpour | |
| 6,083,229 A | 7/2000 | Constantz | |
| 6,099,532 A | 8/2000 | Florea | |
| 6,116,773 A | 9/2000 | Murray | |
| 6,149,655 A | 11/2000 | Constantz | |
| 6,176,607 B1 | 1/2001 | Hajianpour | |
| 6,210,031 B1 | 4/2001 | Murray | |
| 6,302,574 B1 | 10/2001 | Chan | |
| 6,516,977 B2 | 2/2003 | Chan | |
| 6,536,937 B1 | 3/2003 | Burchett | |
| 6,572,256 B2 | 6/2003 | Seaton | |
| 6,592,247 B1 | 7/2003 | Brown | |
| 6,832,703 B1 | 12/2004 | Scott | |
| 6,854,349 B2 | 2/2005 | Brandhorst | |
| 6,874,927 B2 | 4/2005 | Foster | |
| 6,877,891 B2 * | 4/2005 | Hu | 366/247 |
| 6,984,063 B2 | 1/2006 | Barker et al. | |
| 7,029,163 B2 | 4/2006 | Barker | |
| 7,073,936 B1 | 7/2006 | Jonsson | |
| 7,160,020 B2 | 1/2007 | Sand | |

(Continued)

*Primary Examiner* — Brian E. Pellegrino
(74) *Attorney, Agent, or Firm* — Sorell, Lenna & Schmidt, LLP

(57) ABSTRACT

An injectable material delivery device is disclosed and can include a barrel that can have an internal chamber. A plunger can be at least partially disposed within the internal chamber of the barrel. Further, a collapsible mixing blade can be disposed within the internal chamber.

22 Claims, 13 Drawing Sheets

U.S. PATENT DOCUMENTS

| | | |
|---|---|---|
| 2002/0043542 A1 | 4/2002 | Chan |
| 2002/0101784 A1 | 8/2002 | Edwards |
| 2002/0191487 A1 | 12/2002 | Sand |
| 2003/0036762 A1* | 2/2003 | Kerr et al. .................. 606/93 |
| 2003/0067837 A1 | 4/2003 | Seaton |
| 2003/0103408 A1 | 6/2003 | Foster |
| 2003/0112701 A1 | 6/2003 | Burchett |
| 2003/0155381 A1 | 8/2003 | Chan |
| 2003/0231545 A1 | 12/2003 | Seaton |
| 2004/0000203 A1 | 1/2004 | Brandhorst |
| 2004/0049203 A1 | 3/2004 | Scribner |
| 2004/0066706 A1 | 4/2004 | Barker |
| 2004/0196735 A1 | 10/2004 | Barker |
| 2005/0013805 A1 | 1/2005 | Tavori |
| 2005/0105385 A1 | 5/2005 | McGill |
| 2005/0222538 A1 | 10/2005 | Embry |
| 2005/0254340 A1 | 11/2005 | Grebius |
| 2006/0028907 A1 | 2/2006 | Barker |
| 2006/0164913 A1 | 7/2006 | Arramon |
| 2006/0187747 A1 | 8/2006 | Sand |
| 2006/0203608 A1 | 9/2006 | Barker |
| 2006/0250888 A1 | 11/2006 | Foster |
| 2007/0021526 A1 | 1/2007 | He |
| 2007/0027230 A1 | 2/2007 | Beyar |
| 2007/0041267 A1 | 2/2007 | Coffeen |
| 2008/0116224 A1* | 5/2008 | Krueger et al. ............... 222/192 |
| 2011/0085411 A1* | 4/2011 | Henniges et al. ............. 366/190 |

* cited by examiner

INJECTABLE MATERIAL DELIVERY DEVICE WITH AN INTEGRATED MIXER

FIELD OF THE DISCLOSURE

The present disclosure relates generally to orthopedics and orthopedic surgery. More specifically, the present disclosure relates to the delivery of injectable biocompatible materials for treating, repairing, or augmenting bone and other tissue.

BACKGROUND

In human anatomy, the spine is a generally flexible column that can take tensile and compressive loads. The spine also allows bending motion and provides a place of attachment for keels, muscles and ligaments. Generally, the spine is divided into three sections: the cervical spine, the thoracic spine and the lumbar spine. The sections of the spine are made up of individual bones (vertebrae) that are separated from each other by intervertebral discs.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

In order to treat facet joint degeneration or disc degeneration, it can be desirable to inject a biocompatible material into or around the facet joint or disc. After the biocompatible material is injected a surgeon must allow the material to cure in situ or force the material to cure in situ, e.g., apply a curing energy to the material.

DETAILED DESCRIPTION OF THE DRAWINGS

An injectable material delivery device is disclosed and can include a barrel that can have an internal chamber. A plunger can be at least partially disposed within the internal chamber of the barrel. Further, a collapsible mixing blade can be disposed within the internal chamber.

In another embodiment, an injectable material delivery device is disclosed and can include a barrel having a proximal end, a distal end, and an internal chamber. A collapsible mixing blade can be disposed within the internal chamber. The collapsible mixing blade can extend along at least a majority of height of the internal chamber. The injectable material delivery device can also include a drive assembly attached to the distal end of the barrel. The drive assembly can be configured to rotate the collapsible mixing blade within the barrel.

In yet another embodiment, a method of delivering an injectable material to a patient is disclosed and can include loading a first component of the injectable material into an internal chamber of an injectable material delivery device and loading a second component of the injectable material into an internal chamber of an injectable material delivery device. The method can also include sealing the internal chamber of the injectable material delivery device and actuating a mixing motor to rotate a mixing blade within the internal chamber of the injectable material delivery device. The mixing blade can extend along at least a majority of a height of the internal chamber.

In still another embodiment, a mixing blade for an injectable material delivery device is disclosed and can include a base, a plate connected to the base, and a mixing arm that can extend from the plate. The mixing arm can be configured to extend along at least a majority of a height of an internal chamber within the injectable material delivery device.

Description of Relevant Anatomy

Figure 1:
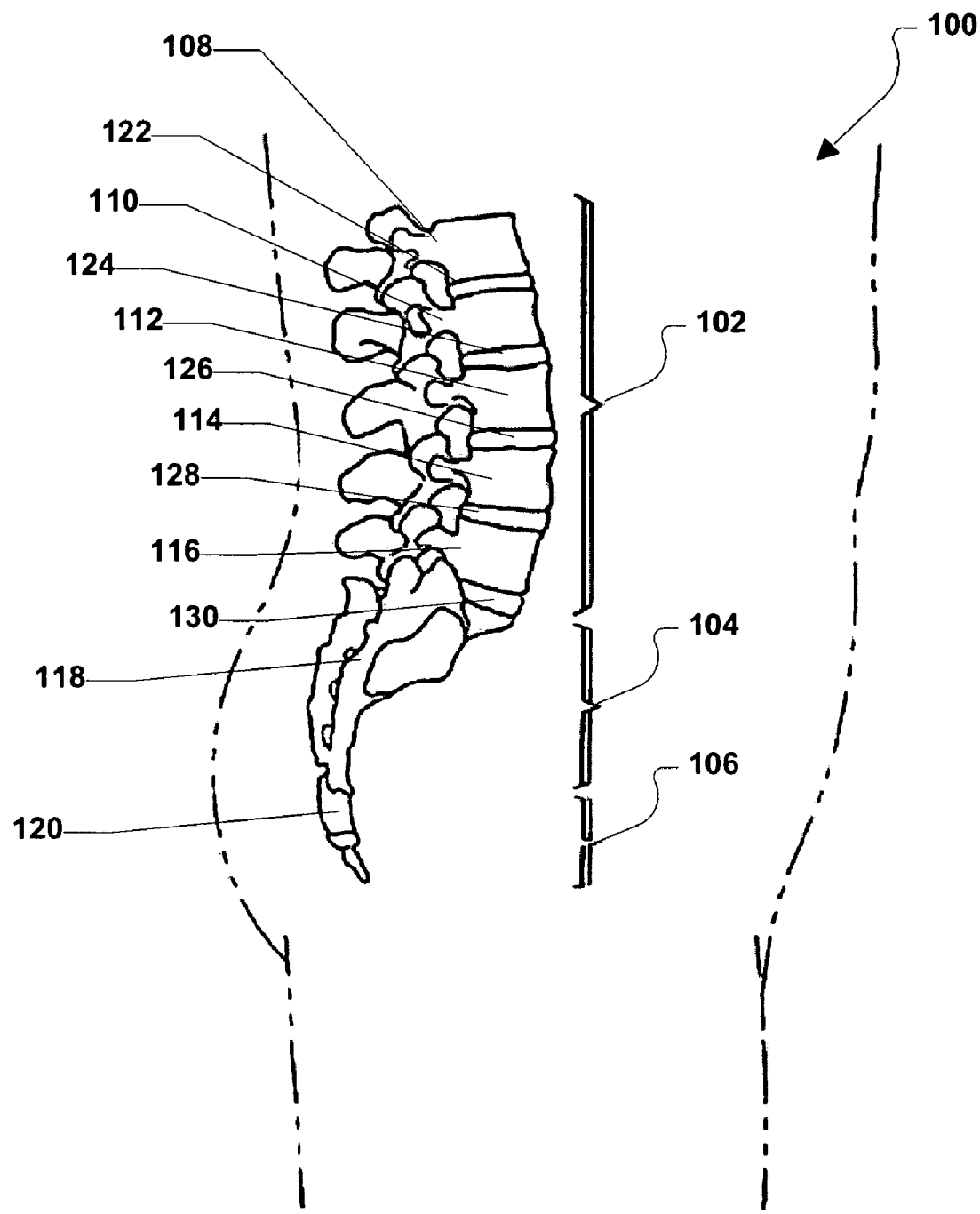
FIG. 1 is a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. As is known in the art, the vertebral column 100 also includes a cervical region and a thoracic region. For clarity and ease of discussion, the cervical region and the thoracic region are not illustrated.

As shown in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, augmentation or treatment, that intervertebral lumbar disc 122, 124, 126, 128, 130 can be treated in accordance with one or more of the embodiments described herein.

Figure 2:
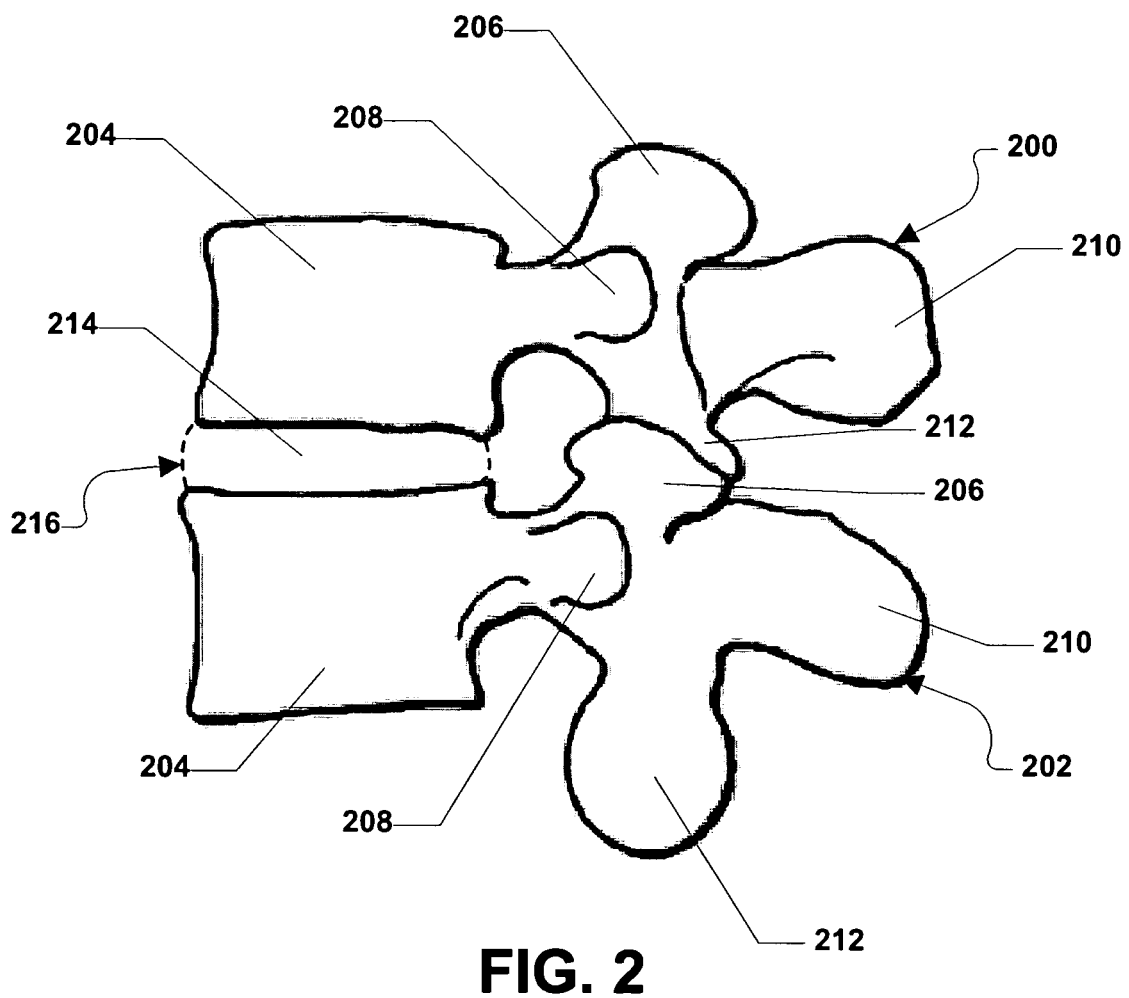
FIG. 2 is a lateral view of a pair of adjacent vertebrae.

FIG. 2 depicts a detailed lateral view of two adjacent vertebrae, e.g., two of the lumbar vertebra 108, 110, 112, 114, 116 shown in FIG. 1. FIG. 2 illustrates a superior vertebra 200 and an inferior vertebra 202. As shown, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202.

Figure 3:
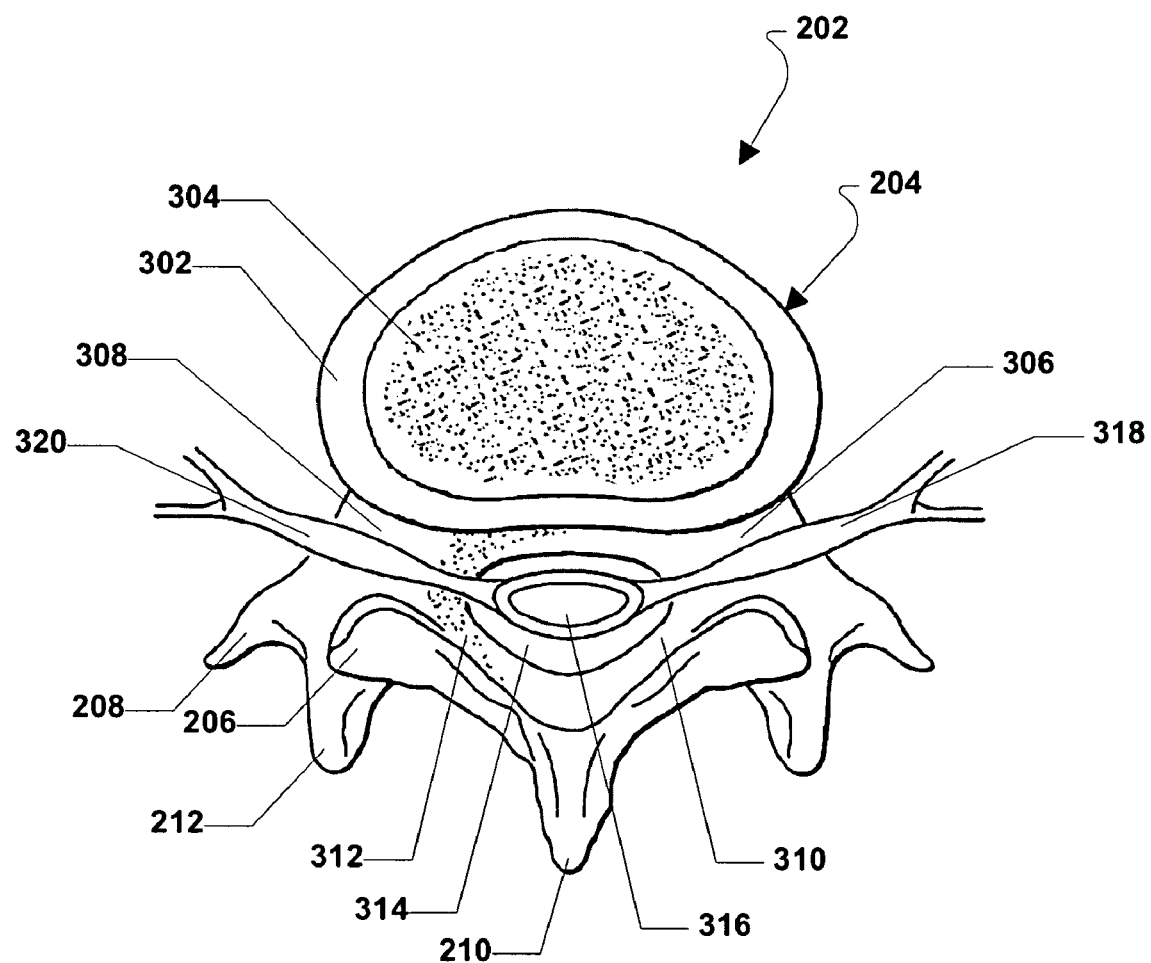
FIG. 3 is a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

In order to treat facet joint degeneration or disc degeneration, it can be desirable to inject a biocompatible material into or around the facet joint or disc. After the biocompatible material is injected a surgeon must allow the material to cure in situ or force the material to cure in situ, e.g., apply a curing energy to the material. It can also be desirable to inject a biocompatible material into or around other bones of a patient.

Description of an Injectable Material Delivery Device

Figure 4:
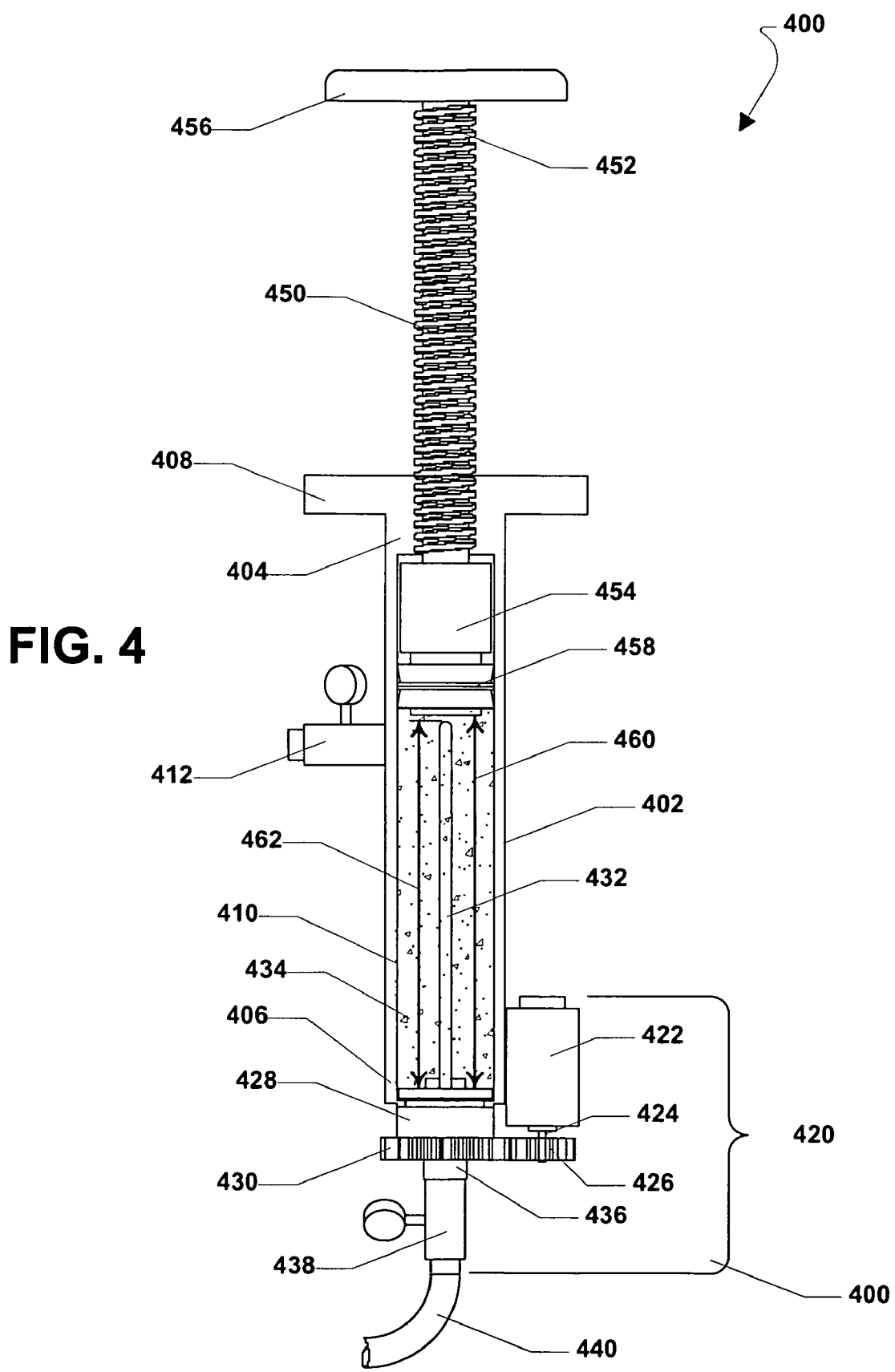
FIG. 4 is a front plan view of an injectable material delivery device.

Referring to FIG. 4, a first embodiment of an injectable material delivery device is shown and is generally designated 400. As illustrated, the device 400 can include a barrel 402 that can define a proximal end 404 and a distal end 406. The proximal end 404 of the barrel 402 can include a barrel handle 408. Further, the barrel 402 can be formed with an internal chamber 410. The injectable material delivery device 400 can also include a first valve 412, or stopcock, situated near the proximal end 404 of the barrel 402. The first valve 412 can provide fluid communication with the internal chamber 410 of the barrel 402.

As shown in FIG. 4, a drive assembly 420 can be attached to, or otherwise integrated with, the distal end 406 of the barrel 402. The drive assembly 420 can include a motor 422 that can be coupled, or otherwise affixed, to the distal end 406 of the barrel 402. The motor 422 can include an output shaft 424 and an output gear 426 can be coupled to, or integrally formed with, the output shaft 424 of the motor 422.

FIG. 4 illustrates that the drive assembly 420 also includes a mixing blade drive hub 428 that can be rotatable affixed to the distal end 406 of the barrel 402. A mixing blade drive gear 430 can be attached to, or integrally formed with, the mixing blade drive hub 428. The mixing blade drive gear 430 can be engaged with the output gear 426 of the motor 422. In a particular embodiment, as the output gear 426 of the motor 422 rotates it can rotate the mixing blade drive gear 430.

As depicted in FIG. 4, a collapsible mixing blade 432 can be disposed within the internal chamber 410 of the barrel 402. In a particular embodiment, the collapsible mixing blade 432 can be at least partially engaged with the mixing blade drive hub 428 and as the collapsible mixing blade hub 428 rotates the collapsible mixing blade 432 can rotate therewith. Further, an injectable material 434 placed within the internal chamber 410 of the barrel 402 can be mixed as the collapsible mixing blade 432 rotates therein. In a particular embodiment, the injectable material 434 can include any biocompatible material that can undergo transformation from a flowable state to a non-flowable state after activation and curing. Further, the injectable material 434 can include one or more polymer materials. For example, the polymer materials can include polyurethane, silicone, silicone polyurethane copolymers, polymethylmethacrylate, epoxy, cyanoacrylate, or a combination thereof.

FIG. 4 shows that the injectable material delivery device 400 can further include a needle hilt 436. In a particular embodiment, the needle hilt 436 can extend from the distal end 406 of the barrel 402 through the mixing blade drive hub 422. Alternatively, the needle hilt 436 can be integrally formed with the mixing blade drive hub 422. Additionally, a second valve 438, or stopcock, can be attached to, or extend from, the needle hilt 436. A material delivery tube 440 can be attached to the second valve 438.

In a particular embodiment, as illustrated in FIG. 4, a plunger 450 can be disposed within the barrel 402 of the injectable material delivery device 400, e.g., within the internal chamber 410 of the barrel 402. The plunger 450 can include a proximal end 452 and a distal end 454. Also, the proximal end 452 of the plunger 450 can include a plunger handle 456 coupled thereto. Moreover, the distal end 454 of the plunger 450 can include a plunger tip 458. In a particular embodiment, at least a portion of the plunger 450 can be formed with external threads. Further, the proximal end 404 of the barrel 402 can be formed with internal threads. Specifically, the barrel handle 408 can be formed with a central opening 458 that can lead to the internal chamber 410 of the barrel 402. The inner wall of central opening 458 within the barrel handle 408 can be formed with internal threads that are sized and shaped to engage the external threads formed on the plunger 450.

The external threads on the plunger 450 can cooperate with the internal threads formed in the barrel 402. As the plunger 450 is rotated relative to the barrel 402 in a first direction, e.g., clockwise, the plunger 450 can advance into the barrel 402. Conversely, as the plunger 450 is rotated relative to the barrel 402 in a second direction opposite the first direction, e.g., counterclockwise, the plunger 450 can retract out of the barrel 402.

In a particular embodiment, the plunger 450 within the internal chamber 410 of the barrel 402 can have a maximum plunger travel distance 460 that is substantially equal to a height of the internal chamber 410 of the barrel 402. In other words, the maximum plunger travel distance 460 can be substantially equal to the distance between a base of the collapsible mixing blade 432 and the plunger tip 458 when the plunger 452 is fully retracted out of the barrel 402. Additionally, the collapsible mixing blade 432 can have a height 462. The height of the collapsible mixing blade 432 can extend along at least a majority of the maximum plunger travel distance 460.

In a particular embodiment, the height 462 of the collapsible mixing blade 432 can be at least seventy percent (70%) of the maximum plunger travel distance 460 of the plunger 450. In another embodiment, the height 462 of the collapsible mixing blade 432 can be at least seventy-five percent (75%) of the maximum plunger travel distance 460 of the plunger 450. In yet another embodiment, the height 462 of the collapsible mixing blade 432 can be at least eighty percent (80%) of the maximum plunger travel distance 460 of the plunger 450. In still another embodiment, the height 462 of the collapsible mixing blade 432 can be at least eighty-five percent (85%) of the maximum plunger travel distance 460 of the plunger 450. In still yet another embodiment, the height 462 of the collapsible mixing blade 432 can be at least ninety percent (90%) of the maximum plunger travel distance 460 of the plunger 450. In another embodiment, the height 462 of the collapsible mixing blade 432 can be at least ninety-five percent (95%) of the maximum plunger travel distance 460 of the plunger 450.

In still another embodiment, the height 462 of the collapsible mixing blade 432 can be at least ninety-six percent (96%) of the maximum plunger travel distance 460 of the plunger 450. In yet another embodiment, the height 462 of the collapsible mixing blade 432 can be at least ninety-seven percent (97%) of the maximum plunger travel distance 460 of the plunger 450. In another embodiment, the height 462 of the collapsible mixing blade 432 can be at least ninety-eight percent (98%) of the maximum plunger travel distance 460 of the plunger 450. In yet another embodiment, the height 462 of the collapsible mixing blade 432 can be at least ninety-nine percent (99%) of the maximum plunger travel distance 460 of the plunger 450.

It can be appreciated that as the plunger 450 is advanced into the barrel 402 of the injectable material delivery device 400, the plunger 450 can collapse the collapsible mixing blade 432. In a particular embodiment, the collapsible mixing blade 432 can be completely collapsed within the barrel 402 by the plunger 450. As such, nearly all of the injectable material 434 can be expressed, or otherwise expelled, from the injectable material delivery device 400.

For example, in a particular embodiment, when the plunger 450 is fully advanced into the barrel 402 at least ninety percent (90%) of the injectable material 434 can be expressed from the injectable material delivery device 400. In another embodiment, at least ninety-one percent (91%) of the injectable material 434 can be delivered when the plunger 450 is fully advanced into the barrel 402. In another embodiment, at least ninety-two percent (92%) of the injectable material 434 can be delivered when the plunger 450 is fully advanced into the barrel 402. In yet another embodiment, at least ninety-three percent (93%) of the injectable material 434 can be delivered when the plunger 450 is fully advanced into the barrel 402. In another embodiment, at least ninety-four percent (94%) of the injectable material 434 can be delivered when the plunger 450 is fully advanced into the barrel 402. In still another embodiment, at least ninety-five percent (95%) of the injectable material 434 can be delivered when the plunger 450 is fully advanced into the barrel 402.

In yet still another embodiment, at least ninety-six percent (96%) of the injectable material 434 can be delivered when the plunger 450 is fully advanced into the barrel 402. In still yet another embodiment, at least ninety-seven percent (97%) of the injectable material 434 can be delivered when the plunger 450 is fully advanced into the barrel 402. In another embodiment, at least ninety-eight percent (98%) of the injectable material 434 can be delivered when the plunger 450 is fully advanced into the barrel 402. In yet another embodiment, at least ninety-nine percent (99%) of the injectable material 434 can be delivered when the plunger 450 is fully advanced into the barrel 402.

DESCRIPTION OF A FIRST EMBODIMENT OF A COLLAPSIBLE MIXING BLADE

Figure 5:
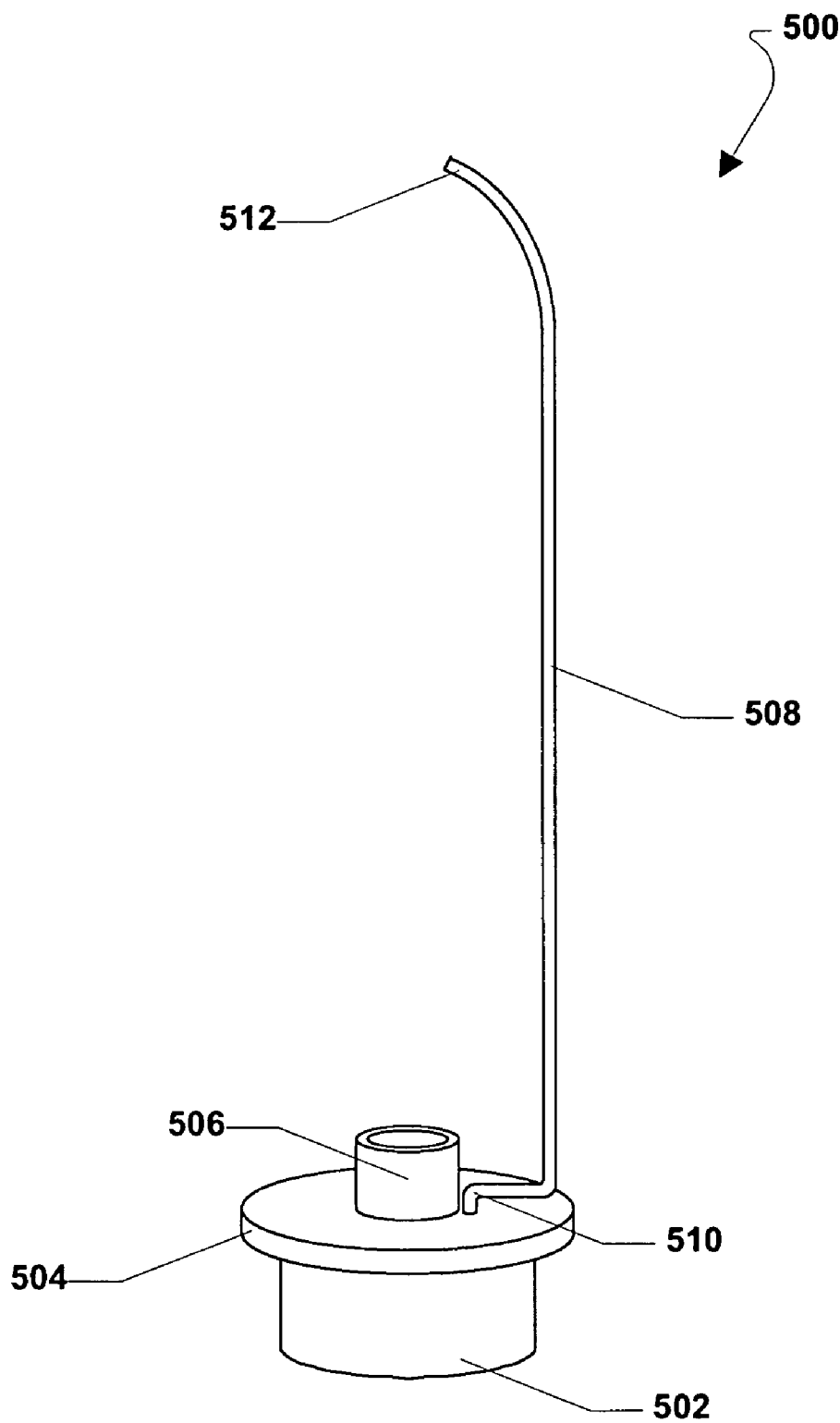
FIG. 5 is a perspective view of a first embodiment of a collapsible mixing blade.

Referring now to FIG. 5, a first embodiment of a collapsible mixing blade is shown and is generally designated 500. In a particular embodiment, the collapsible mixing blade 500 can be installed within an injectable material delivery device, e.g., the injectable material delivery device 400 described above.

As shown, the collapsible mixing blade 500 can include a base 502. In a particular embodiment, the base 502 can be generally cylindrical and hollow. Further, as illustrated, a flat, generally cylindrical plate 504 can be attached to, or integrally formed with, the top of the base 502. FIG. 5 also shows that a central hub 506 can extend from the top of plate 504 in a direction that is substantially opposite the base 502. In a particular embodiment, the central hub 506 can be hollow and generally cylindrical. Further, the central hub 506 can provide fluid communication into the base 502 of the collapsible mixing blade 500.

FIG. 5 further depicts a mixing arm 508 extending from the plate 504 in substantially the same direction as the central hub 506. The mixing arm 508 can include a first end 510 and a second end 512. As shown, the first end 510 of the mixing arm 508 can be attached to the plate 504. The second end 512 of the mixing arm 508 can be free, i.e., not connected to anything. As such, the mixing arm 508 is generally shaped like a whip or a lash. As the collapsible mixing blade 500 rotates, the mixing arm 508 can whip around and mix an injectable material within the injectable material delivery device in which the collapsible mixing blade 500 is installed.

The mixing arm 508 can be substantially elastic and the mixing arm 508 can be collapsed, or otherwise compressed, onto the plate 504 by a plunger within the injectable material delivery device. Accordingly, the mixing arm 508 can be moved between an extended configuration, in which the mixing arm 508 substantially upright on the plate 504, and a collapsed configuration, in which the mixing arm 508 is collapsed onto the plate 504 by the plunger. When a compressive force provided by the plunger is removed from the mixing arm 508, the mixing arm 508 can return to the extended configuration.

In a particular embodiment, the collapsible mixing blade 500 can be made from one or more polymer materials. The polymer materials can include polyurethane materials, polyolefin materials, polyaryletherketone (PAEK) materials, or a combination thereof. Further, the polyolefin materials can include polypropylene, polyethylene, halogenated polyolefin, flouropolyolefin, or a combination thereof. The (PAEK) materials can include polyetherketone (PEK), polyetheretherketone (PEEK), polyetherketoneketone (PEKK), polyetherketoneetherketoneketone (PEKEKK), or a combination thereof.

DESCRIPTION OF A SECOND EMBODIMENT OF A COLLAPSIBLE MIXING BLADE

Figure 6:
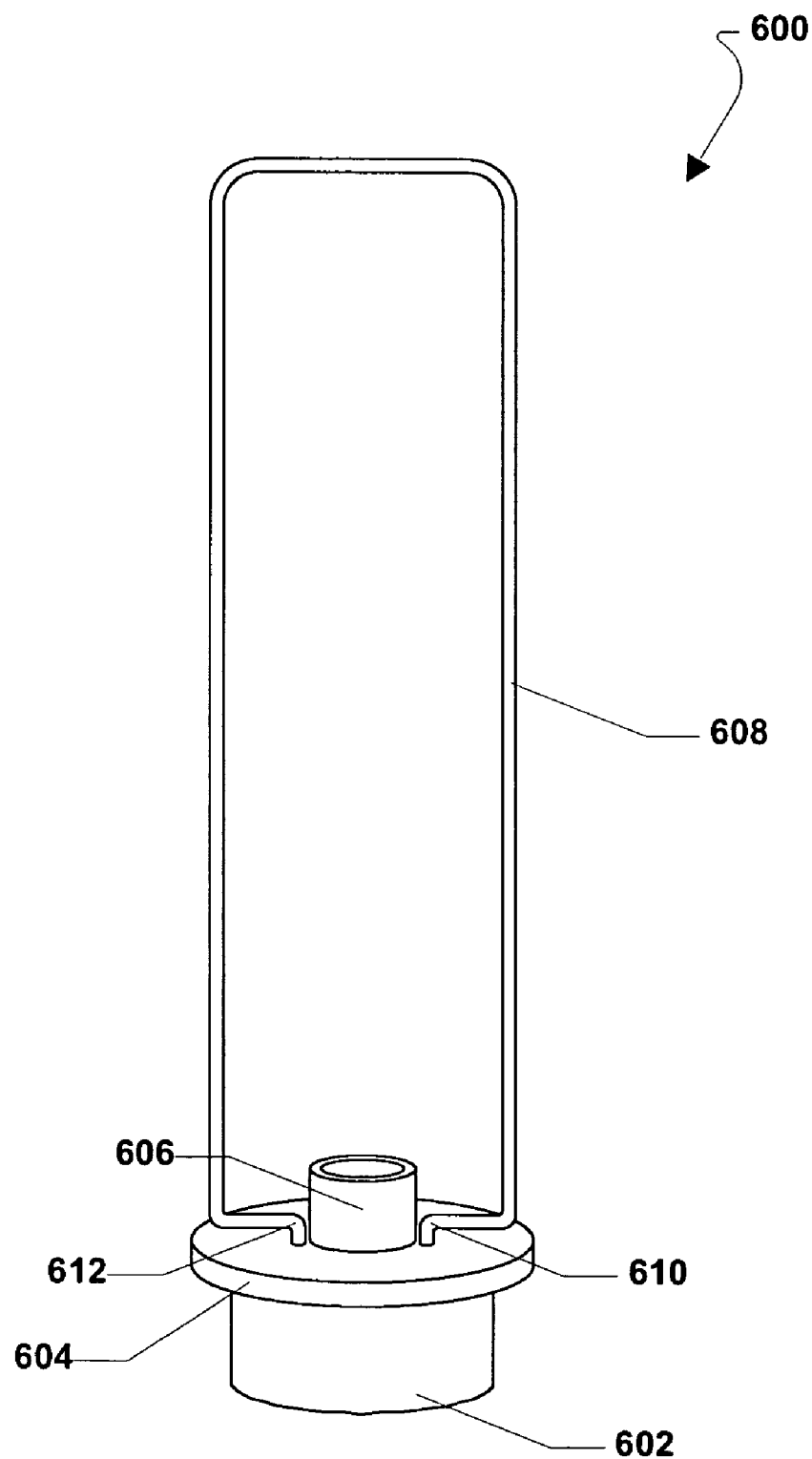
FIG. 6 is a perspective view of a second embodiment of a collapsible mixing blade.

Referring now to FIG. 6, a second embodiment of a collapsible mixing blade is shown and is generally designated 600. In a particular embodiment, the collapsible mixing blade 600 can be installed within an injectable material delivery device, e.g., the injectable material delivery device 400 described above.

As shown, the collapsible mixing blade 600 can include a base 602. In a particular embodiment, the base 602 can be generally cylindrical and hollow. Further, as illustrated, a flat, generally cylindrical plate 604 can be attached to, or integrally formed with, the top of the base 602. FIG. 6 also shows that a central hub 606 can extend from the top of plate 604 in a direction that is substantially opposite the base 602. In a particular embodiment, the central hub 606 can be hollow and generally cylindrical. Further, the central hub 606 can provide fluid communication into the base 602 of the collapsible mixing blade 600.

FIG. 6 further depicts a mixing arm 608 extending from the plate 604 in substantially the same direction as the central hub 606. The mixing arm 608 can include a first end 610 and a second end 612. As shown, the first end 610 of the mixing arm 608 can be attached to the plate 604. Also, the second end 612 of the mixing arm 608 can be attached to the plate 604. As such, the mixing arm 608 can form a generally U-shape with the base of the U distanced from the plate 604. In a particular embodiment, as the collapsible mixing blade 600 rotates, the mixing arm 608 can whip around and mix an injectable material within the injectable material delivery device in which the collapsible mixing blade 600 is installed.

The mixing arm 608 can be substantially elastic and the mixing arm 608 can be collapsed, or otherwise compressed, onto the plate 604 by a plunger within the injectable material delivery device. Accordingly, the mixing arm 608 can be moved between an extended configuration, in which the mixing arm 608 substantially upright on the plate 604, and a collapsed configuration, in which the mixing arm 608 is collapsed onto the plate 604 by the plunger. When a compressive force provided by the plunger is removed from the mixing arm 608, the mixing arm 608 can return to the extended configuration.

In a particular embodiment, the collapsible mixing blade 600 can be made from one or more polymer materials. The polymer materials can include polyurethane materials, polyolefin materials, polyaryletherketone (PAEK) materials, or a combination thereof. Further, the polyolefin materials can include polypropylene, polyethylene, halogenated polyolefin, flouropolyolefin, or a combination thereof. The (PAEK) materials can include polyetherketone (PEK), polyetheretherketone (PEEK), polyetherketoneketone (PEKK), polyetherketoneetherketoneketone (PEKEKK), or a combination thereof.

Description of a First Method of Using an Injectable Material Delivery Device

Figure 7:
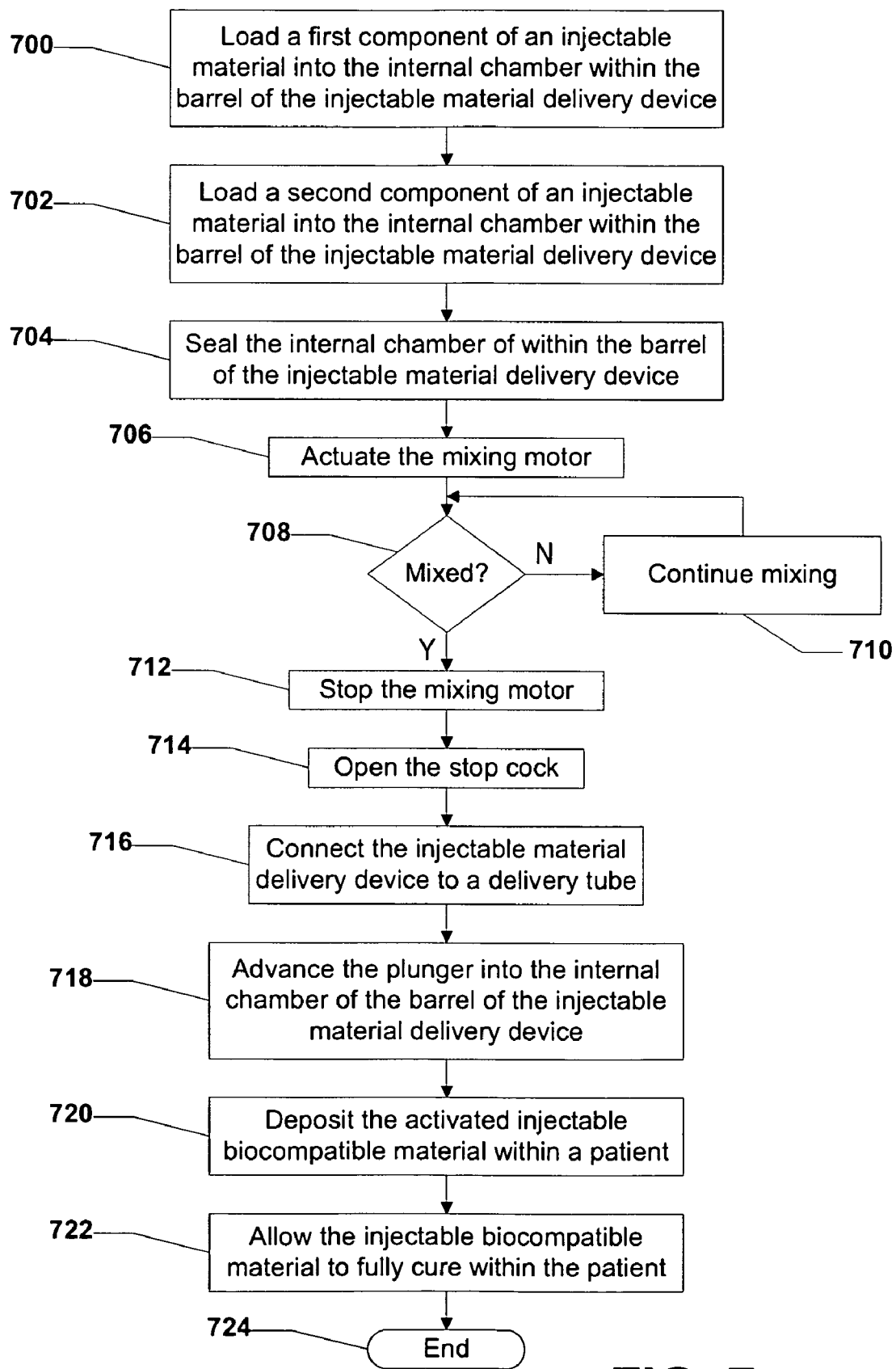
FIG. 7 is a flow chart illustrating a first method of using an injectable material delivery device.

Referring to FIG. 7, a first method of using an injectable material delivery device is shown and commences at block 700. At block 700, a first component of an injectable material can be loaded into an internal chamber within a barrel of the injectable material delivery device. At block 702, a second component of the injectable material can be loaded into the internal chamber of the barrel of the injectable material delivery device. Moving to block 704, the internal chamber of the barrel of the injectable material delivery device can be sealed, e.g., by closing a first valve, or stopcock, that provides fluid communication with the barrel.

At block 706, a motor of the injectable material delivery device can be actuated. In a particular embodiment, actuating the motor can cause a collapsible mixing blade to rotate within the barrel. The collapsible mixing blade can whip around within the barrel and mix the injectable material therein.

Proceeding to decision step 708, a user can determine whether the injectable material is thoroughly, or properly, mixed. If not, the method can proceed to block 710 and the injectable material delivery device can be used to continue mixing the injectable material. If the injectable material is properly mixed, the method can move to block 712 and the motor can be stopped. Thereafter, the injectable material delivery device can be connected to a delivery tube at block 714.

Moving to block 716, a second valve, or stopcock, can be opened to provide fluid communication between the barrel and the delivery tube. At block 718, a plunger on the injectable material delivery device can be advanced into the internal chamber of the barrel. Further, at block 720, the injectable material can be deposited within a patient. Thereafter, at block 722, the injectable material can be cured within the patient. The injectable material can be cured by allowing the material to cure naturally or by exposing the injectable material to an energy source, e.g., a heat source, a light source, or combination thereof. The method can then end at state 724.

Description of a Second Injectable Material Delivery Device

Figure 8:
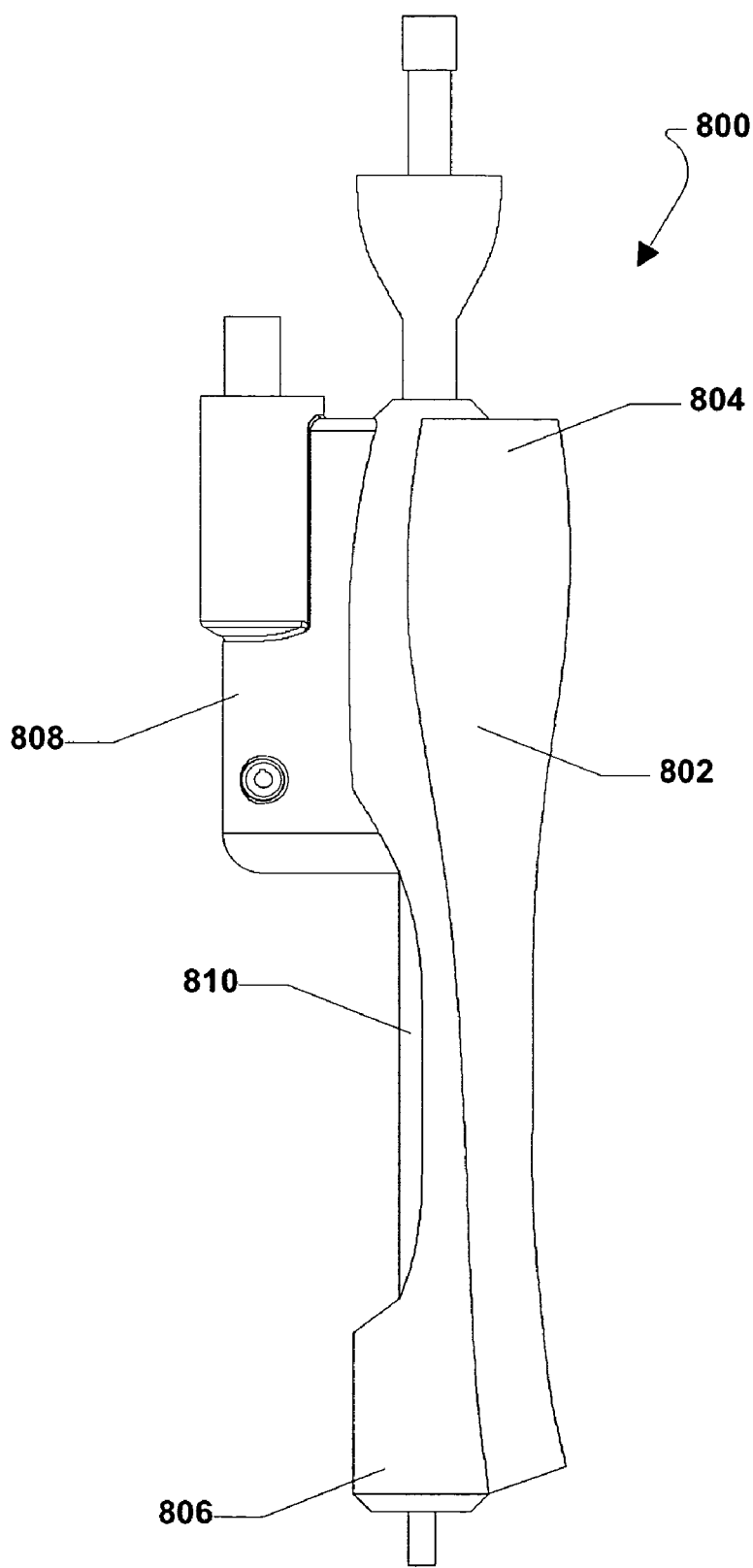
FIG. 8 is a side plan view of a second embodiment of an injectable material delivery device.
Figure 9:
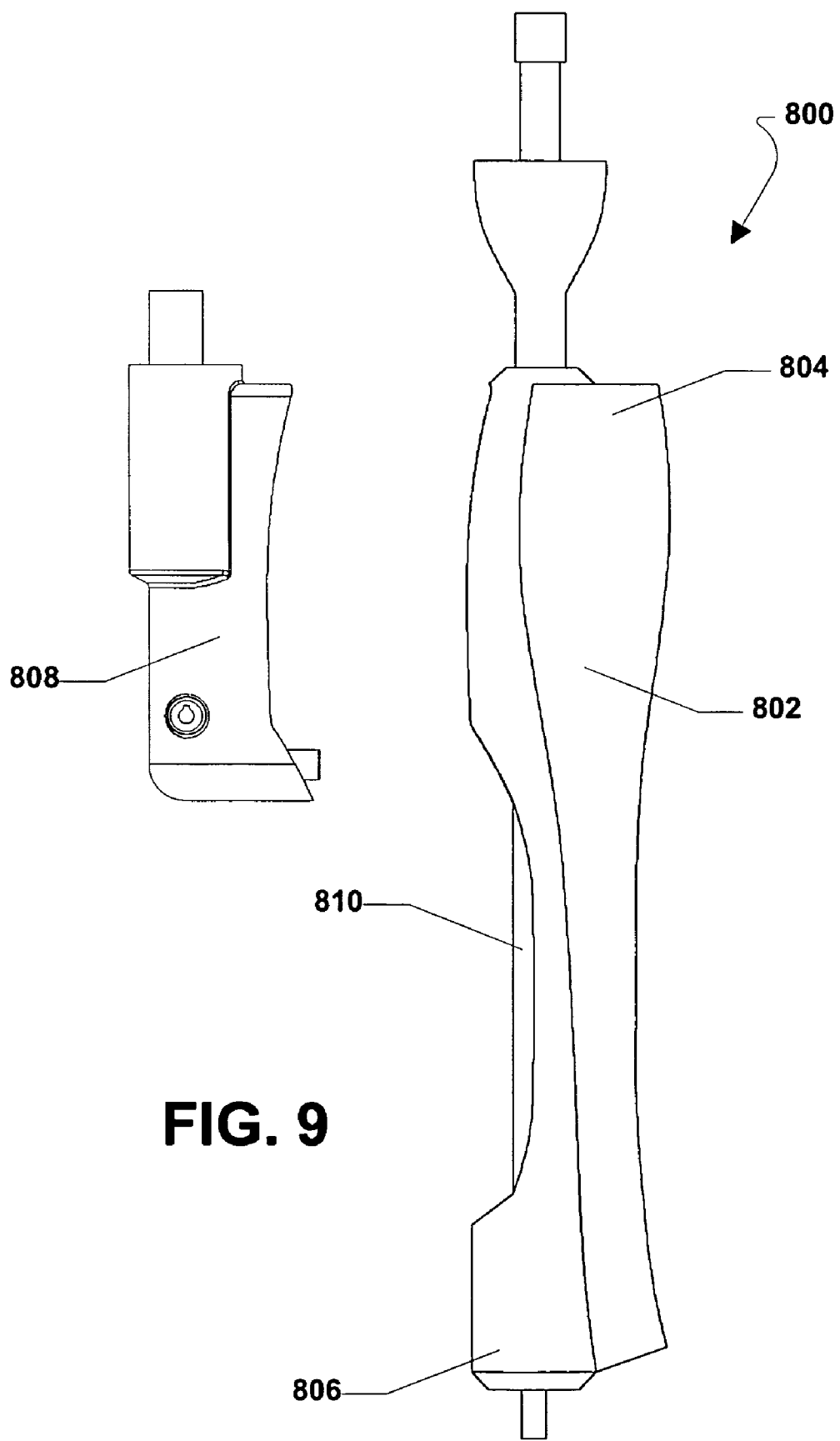
FIG. 9 is an exploded side plan view of the second injectable material delivery device.
Figure 10:
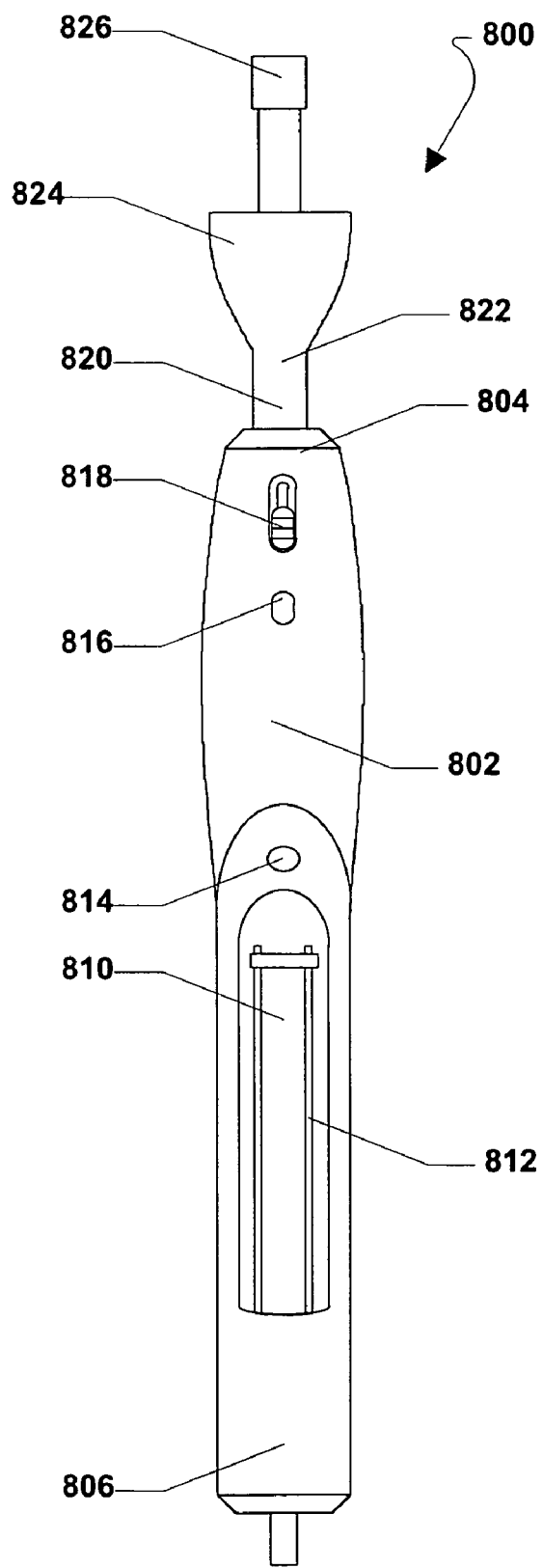
FIG. 10 is a front plan view of the second injectable material delivery device.

Referring to FIG. 8 through FIG. 10, a second embodiment of an injectable material delivery device is shown and is generally designated 800. As illustrated, the device 800 can include a housing 802 that can define a proximal end 804 and a distal end 806. A cartridge 808 can be removably engaged with the proximal end 804 of the housing 802. The cartridge 808 is described in detail below.

FIG. 10 indicates that the housing 802 can be formed with an internal chamber 810. A collapsible mixing blade 812 can be disposed within the internal chamber 810 of the housing 802. The collapsible mixing blade 812 is described in detail below. The collapsible mixing blade 812 can be engaged with a drive assembly (not shown) that is also located within the housing 802, e.g., near the distal end 806 of the housing 802.

In a particular embodiment, the collapsible mixing blade 812 can rotate within the internal chamber 810 of the housing 802. An injectable material placed within the internal chamber 810 of the housing 802 can be mixed as the collapsible mixing blade 812 rotates therein. In a particular embodiment, the injectable material can include any biocompatible material that can undergo transformation from a flowable state to a non-flowable state after activation and curing. Further, the injectable material can include one or more polymer materials. For example, the polymer materials can include polyurethane, silicone, silicone polyurethane copolymers, polymethylmethacrylate, epoxy, cyanoacrylate, or a combination thereof.

FIG. 10 further shows that the housing 802 can include a port 814 that can provide fluid communication with the internal chamber 810 of the housing 802. The cartridge 808, e.g., a tube extending from the cartridge 808, can extend into the port 814 when the cartridge 808 is engaged with the housing 802 as shown in FIG. 8. When an ampoule within the cartridge 808 is broken, the fluid within the ampoule can flow into the internal chamber 810 of the housing 802. The fluid from the ampoule can be mixed with one or more ingredients that may already be present within the internal chamber 810 of the housing 802.

As shown in FIG. 10, the injectable material delivery device 800 can also include a switch 816 and an indicator light 818. The switch 816 can be slid, or otherwise toggled, in order to energize the injectable material delivery device 800 and commence a mixing process within the injectable material delivery device 800. The indicator light 818 can indicate the stages of the mixing process. For example, the indicator light 818 can glow red to indicate that the injectable material delivery device 800 is mixing a material therein. Thereafter, the indicator light 818 can glow orange to indicate that the mixing is finished and the material is setting, e.g., by waiting a predetermined time period. Once the predetermined time period elapses, the indicator light 818 can glow green in order to indicate that the material therein is ready to be tested to determine the viscosity of the material.

FIG. 8 through FIG. 10 illustrate a plunger 820 engaged with the housing 802 of the injectable material delivery device 800. The plunger 820 can extend into the internal chamber 810 of the housing 802. The plunger 820 can include a proximal end 822 and a distal end (not shown). The proximal end 822 of the plunger 820 can include a plunger handle 824. A priming button 826 can extend from the plunger 820, e.g., through the plunger handle 824. The priming button 826 can be depressed into the plunger handle 824 in order to prime the injectable material delivery device 800 prior to expelling material from the injectable material delivery device 800. Priming the device 800 can include moving a plunger tip (not shown) into contact within the material within the injectable material delivery device 800 and expressing an air, or fumes, within the device 800 from within the internal chamber 810.

After the device 800 is primed, the plunger 820 can be slid into the internal chamber 810 of the housing 802 in order to express the material from the injectable material delivery device 800. As the plunger 820 is moved into the internal chamber 810, the plunger 820 can collapse the collapsible mixing blade 812. In a particular embodiment, the collapsible mixing blade 812 can be completely collapsed within the internal chamber 810 of the housing 802 by the plunger 820. As such, nearly all of the injectable material within the internal chamber 810 can be expressed, or otherwise expelled, from the injectable material delivery device 800.

Description of a Cartridge

Figure 11:
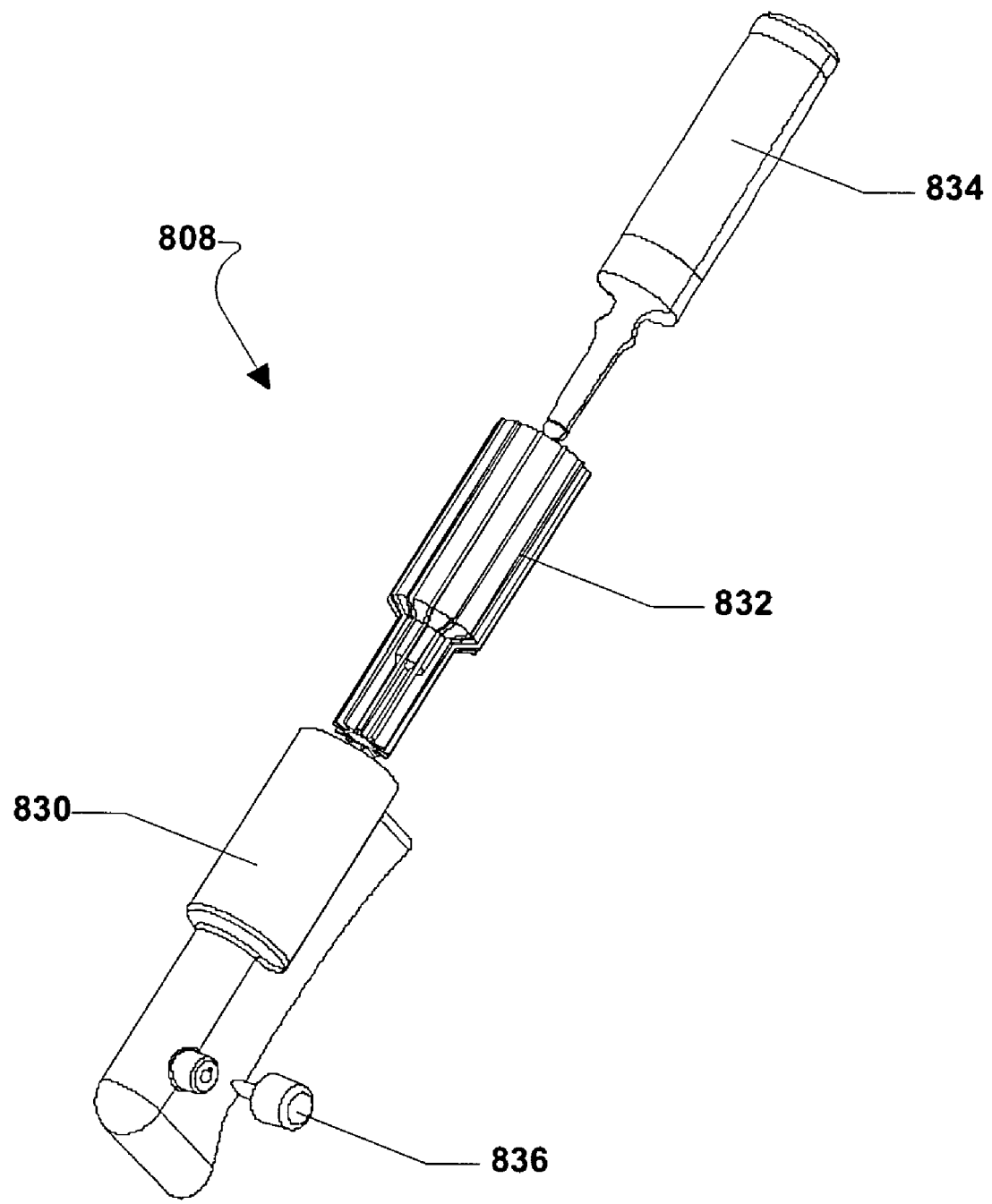
FIG. 11 is an exploded perspective view of a cartridge for the second injectable material delivery device.

Referring now to FIG. 11, details concerning the cartridge 808 are illustrated. FIG. 11 indicates that the cartridge 808 can include an outer liner 830 that is formed within an internal chamber (not shown). Further, an inner liner 832 can fit into the internal chamber of the outer liner 830. The inner liner 832 can also be formed with an internal chamber (not show) and an ampoule 834 can be disposed within the internal chamber of the inner liner 832. The cartridge 808 can also include a pin 836. The pin 836 can extend through the outer liner 830 and into the inner liner 832. The pin 836 can be depressed into the cartridge 808 in order to break the tip of the ampoule 834. Once the tip of the ampoule 834 is broken, fluid within the ampoule 834 can flow out of the cartridge and into an injectable material delivery device.

DESCRIPTION OF A THIRD EMBODIMENT OF A COLLAPSIBLE MIXING BLADE

Figure 12:
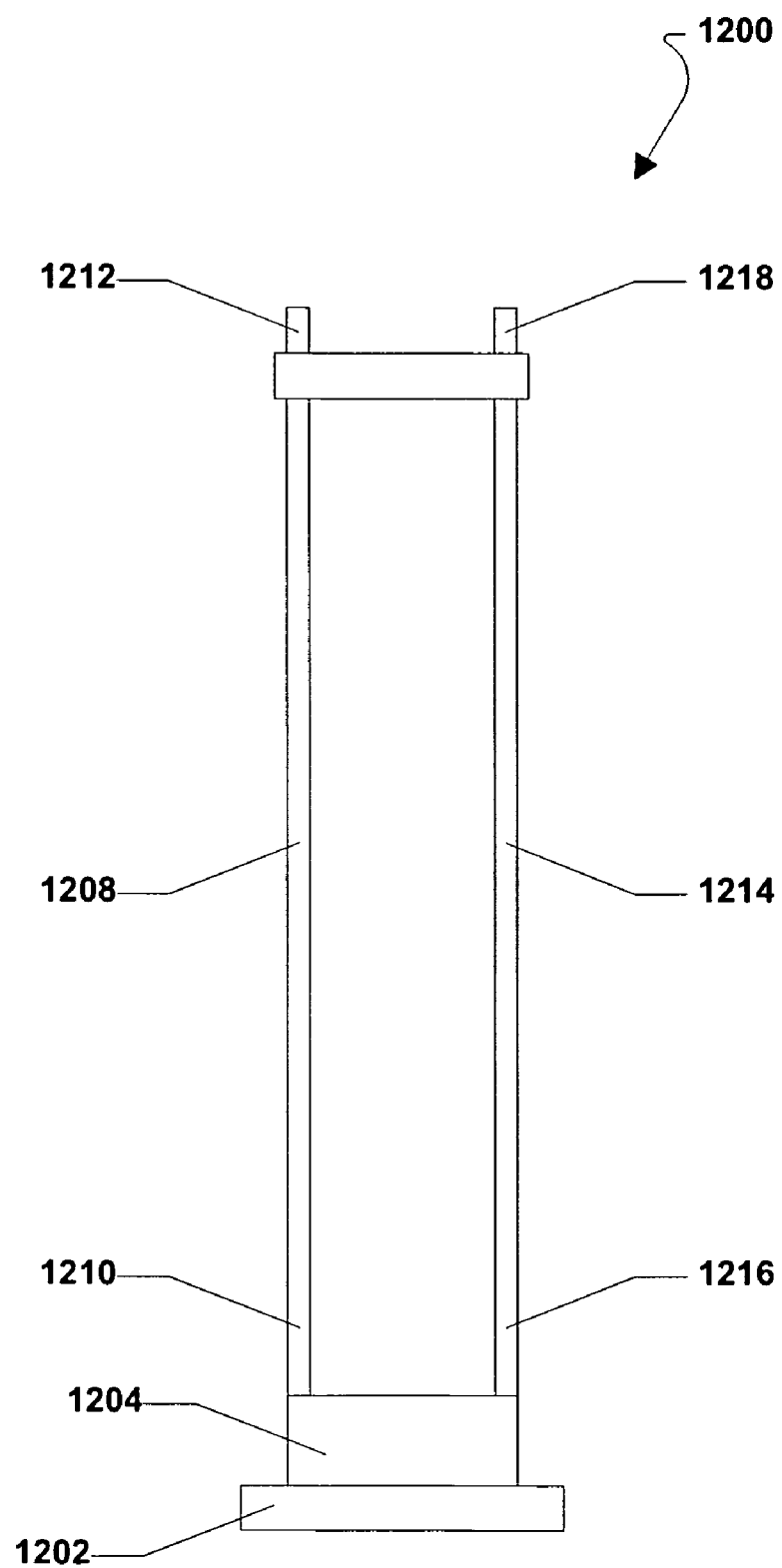
FIG. 12 is a plan view of a third embodiment of a collapsible mixing blade.

Referring now to FIG. 12, a third embodiment of a collapsible mixing blade is shown and is generally designated 1200. In a particular embodiment, the collapsible mixing blade 1200 can be installed within an injectable material delivery device, e.g., the injectable material delivery device 800 described above.

As shown, the collapsible mixing blade 1200 can include a base 1202. In a particular embodiment, the base 1202 can be generally disk shaped and formed with a central opening (not shown). Further, as illustrated, a central hub 1204 can extend from the base 1202. In a particular embodiment, the central hub 1204 can be hollow and generally cylindrical. Further, the central hub 1204 can provide fluid communication into the base 1202 of the collapsible mixing blade 1200.

FIG. 12 further depicts a first mixing arm 1208 extending from the plate 1204 in substantially the same direction as the central hub 1204. The first mixing arm 1208 can include a first end 1210 and a second end 1212. As shown, the first end 1210 of the mixing arm 1208 can be attached to the central hub 1204.

A second mixing arm 1214 can also extend from the plate 1204 in substantially the same direction as the first mixing arm 1208. The second mixing arm 1214 can include a first end 1216 and a second end 1218. As shown, the first end 1216 of the second mixing arm 1214 can be attached to the central hub 1204.

In a particular embodiment, the second end 1212 of the first mixing arm 1208 and the second end 1218 of the second mixing arm 1214 can be attached to a paddle 1220. As the collapsible mixing blade 1200 rotates, the mixing arms 1208, 1214 can twist around each other causing the length of the collapsible mixing blade 1200 to decrease. As such, the paddle 1220 can move toward the base 1202 of the collapsible mixing blade 1200.

Further, the mixing arms 1208, 1214 can be substantially elastic and the mixing arms 1208, 1214 can be collapsed, or otherwise compressed, onto the central hub 1204 by a plunger within the injectable material delivery device. Accordingly, the mixing arms 1208, 1214 can be moved between an extended configuration, in which the mixing arms 1208, 1214 are substantially upright on the central hub 1204, and a collapsed configuration, in which the mixing arms 1208, 1214 are collapsed onto the central hub 1204 by the plunger. When a compressive force provided by the plunger is removed from the mixing arms 1208, 1214, the mixing arms 1208, 1214 can return to the extended configuration.

In a particular embodiment, the collapsible mixing blade 1200 can be made from one or more polymer materials. The polymer materials can include polyurethane materials, polyolefin materials, polyaryletherketone (PAEK) materials, or a combination thereof. Further, the polyolefin materials can include polypropylene, polyethylene, halogenated polyolefin, flouropolyolefin, or a combination thereof. The (PAEK) materials can include polyetherketone (PEK), polyetheretherketone (PEEK), polyetherketoneketone (PEKK), polyetherketoneetherketoneketone (PEKEKK), or a combination thereof.

Description of a Second Method of Using an Injectable Material Delivery Device

Figure 13:
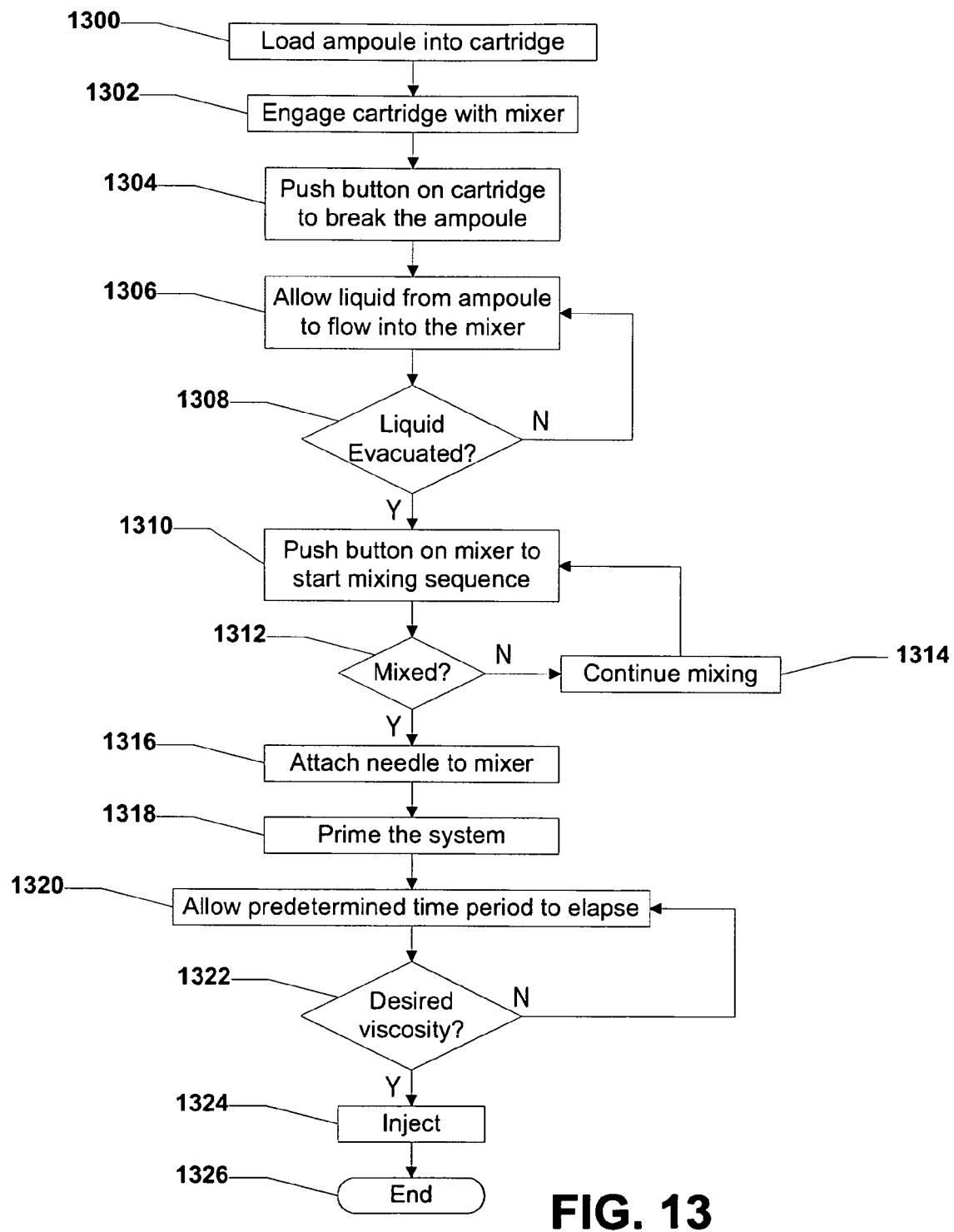
FIG. 13 is a flow chart illustrating a second method of using an injectable material delivery device.

Referring to FIG. 13, a method of using an injectable material delivery device is shown and commences at block 1300. At block 1300, an ampoule can be loaded into a cartridge. At block 1302, the cartridge can be engaged with a mixer. Thereafter, at block 1304, a button on the cartridge can be pushed in order to break the ampoule.

Moving to block 1306, the liquid from the ampoule can be allowed to flow into the mixer. The liquid can be combined with one or more additional ingredients that are already present within the mixer. At decision step 1308, it can be determined whether all of the liquid is evacuated from the ampoule. If not, the method can return to block 1306 and continue as described herein. If all of the liquid is evacuated, the method can proceed to block 1310. At block 1310, a power button on the mixer can be pushed, or otherwise toggled, in order to start a mixing sequence within the mixer.

Continuing to block 1314, it can be determined whether the material within the mixer is mixed. If not, the method can move to block 1314 and the mixer can be allowed to continue mixing. If the material is mixed, the method can move to block 1316 and a needle can be attached to the mixer. Thereafter, at block 1318, the system can be primed, e.g., by letting some of the material to flow into the needle.

At block 1320, a predetermined time period can be allowed to elapse. During this time, a light on the mixer can glow a particular color, e.g., orange, to indicate to the user to wait. When the light turns to another color, e.g., green, the time period has elapsed. Moving to decision step 1322, it can be determined whether the desired viscosity has been reached. If the desired viscosity is not reached, the method can return to block 1320 and continue as described. On the other hand, if the desired viscosity is reached, the method can proceed to block 1324 and the material can be injected, e.g., into a patient. Thereafter, at state 1326, the method can end.

Conclusion

With the configuration of structure described above, the injectable material delivery device provides a device that can be used to mix an injectable material placed therein. The collapsible mixing blade extends within the injectable material delivery device and can readily mix an injectable material placed therein. After, the injectable material is mixed the injectable material delivery device can be used to deliver the material to a patient, e.g., within or around bony tissue. For example, the injectable material can be injected into, around, or into and around, a disc, a facet bone, or other bone along a spinal column. Further, the injectable material can be injected into, around, or into and around other bones or joints that make up a human skeleton. As a plunger within the delivery device is advanced into the delivery device, the collapsible mixing blade can collapse to allow nearly all of the injectable material to be delivered to the patient.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An injectable material delivery device, comprising:
   a barrel having an internal chamber;
   a plunger at least partially disposed within the internal chamber of the barrel;
   a collapsible mixing blade within the internal chamber, the collapsible mixing blade comprising:
     a base having a top and a bottom;
     a plate having a top and a bottom, with the bottom of the plate connected to the top of the base; and
     a collapsible mixing arm with a first end extending from the top of the plat;
   a drive assembly integrated with a distal end of the barrel, the drive assembly comprises:
     a motor;
     an output shaft extending from the motor;
     an output gear connected to the output shaft;
     a mixing blade drive gear meshed with the output gear; and
     a mixing blade drive hub connected to the mixing blade drive gear, wherein the mixing blade drive hub is coupled to the collapsible mixing blade;
   a needle hilt integrally formed with the mixing blade drive hub; and
   a valve extending from the needle hilt and configured for attachment with a material delivery tube,
   wherein the drive assembly is configured to rotate the collapsible mixing blade within the barrel.

2. The injectable material delivery device of claim 1, wherein a height of the collapsible mixing blade is at least seventy percent (70%) of a maximum plunger travel distance of the plunger.

3. The injectable material delivery device of claim 2, wherein a height of the collapsible mixing blade is at least eighty-five percent (85%) of a maximum plunger travel distance of the plunger.

4. The injectable material delivery device of claim 3, wherein a height of the collapsible mixing blade is at least ninety-nine percent (99%) of a maximum plunger travel distance of the plunger.

5. The injectable material delivery device of claim 1 wherein at least ninety percent (90%) of an injectable material within the injectable material delivery device can be expressed from the injectable material delivery device when the plunger is fully advanced into the barrel.

6. The injectable material delivery device of claim 5, wherein at least ninety-five percent (95%) of an injectable material within injectable material delivery device can be expressed from the injectable material delivery device when the plunger is fully advanced into the barrel.

7. The injectable material delivery device of claim 6, wherein at least ninety-nine percent (99%) of an injectable material within injectable material delivery device can be expressed from the injectable material delivery device when the plunger is fully advanced into the barrel.

8. A method of delivering an injectable material to a patient, the method comprising: providing the injectable material delivery device of claim 1, loading a first component of the injectable material into said internal chamber of an injectable material delivery device; loading a second component of the injectable material into said internal chamber of said injectable material delivery device; sealing the internal chamber of the injectable material delivery device; and actuating said motor to rotate said blade within the internal chamber of the injectable material delivery device, wherein the mixing blade extends along at least a majority of a height of the internal chamber.

9. The method of claim 8, further comprising: stopping the mixing motor when the injectable material is mixed.

10. The method of claim 9, further comprising: connecting the injectable material delivery device to a delivery tube.

11. The method of claim 10, further comprising: advancing a plunger of the injectable material delivery device into the internal chamber to collapse the mixing blade and express the injectable material from the internal chamber.

12. An injectable material delivery device, comprising:
   a barrel having a proximal end, a distal end, and an internal chamber;
   a collapsible mixing blade disposed within the internal chamber, wherein the collapsible mixing blade extends along at least a majority of height of the internal chamber;
   a drive assembly integrally attached to the distal end of the barrel, the drive assembly comprises:
     a motor;
     an output shaft extending from the motor;
     an output gear connected to the output shaft;
     a mixing blade drive gear meshed with the output gear; and
     a mixing blade drive hub connected to the mixing blade drive gear, wherein the mixing blade drive hub is coupled to the collapsible mixing blade;
   a needle hilt integrally formed with the mixing blade drive hub; and a valve extending from the needle hilt and configured for attachment with a material delivery tube, wherein the drive assembly is configured to rotate the collapsible mixing blade within the barrel.

13. The injectable material delivery device of claim 12, wherein the output gear, the mixing blade, and the mixing blade drive hub are configured to transmit rotary motion from the motor to the collapsible mixing blade.

14. The injectable material delivery device of claim 12, wherein the collapsible mixing blade comprises:
   a base;
   a plate connected to the base; and
   a mixing arm extending from the plate, wherein the mixing arm extends along at least a majority of a height of the internal chamber.

15. The injectable material delivery device of claim 14, wherein the arm comprises:
   a first end connected to the plate; and
   a second end that is free.

16. The injectable material delivery device of claim 15, wherein the arm is generally whip-shaped.

17. The injectable material delivery device of claim 14, wherein the arm comprises: a first end connected to the plate; and a second end connected to the plate.

18. The injectable material delivery device of claim 17, wherein the arm is generally U-shaped.

19. The injectable material delivery device of claim 12, further comprising:
   a plunger at least partially disposed within the internal chamber, wherein the collapsible mixing blade is configured to collapse as the plunger is advanced into the internal chamber of the barrel.

20. A delivery device, for delivering injectable material comprising:
   a base having a top and a bottom;
   a plate having a top and a bottom, with the bottom of the plate connected to the top of the base;
   a collapsible mixing arm with a first end extending from the top of the plate, wherein the collapsible mixing arm is configured to move between an extended configuration in which the mixing arm is substantially upright to extend along at least a majority of a height of an internal chamber within the injectable material delivery device and a collapsed configuration in which the mixing arm is collapsed, or substantially compressed, onto the top of the plate;
   a drive assembly integrally attached to the injectable material delivery device, the drive assembly comprises:
      a motor;
      an output shaft extending from the motor;
      an output gear connected to the output shaft;
      a mixing blade drive gear meshed with the output gear; and
      a mixing blade drive hub connected to the mixing blade drive gear, wherein the mixing blade drive hub is coupled to the collapsible mixing blade; and
   a needle hilt integrally formed with the mixing blade drive hub,
   wherein the drive assembly is configured to rotate the collapsible mixing blade within the barrel.

21. The delivery device of claim 20, wherein the arm further comprises:
   a second end that is free.

22. The delivery device of claim 21, wherein the arm is generally whip-shaped.

* * * * *